US012806192B2

(12) United States Patent
Smith

(10) Patent No.: US 12,806,192 B2
(45) Date of Patent: Nov. 24, 2026

(54) ENDOCRINE THERAPY AND ABEMACICLIB COMBINATION FOR THE ADJUVANT TREATMENT OF NODE-POSITIVE, EARLY STAGE, HORMONE RECEPTOR-POSITIVE, HUMAN EPIDERMAL GROWTH FACTOR RECEPTOR 2-NEGATIVE BREAST CANCER

(71) Applicant: Eli Lilly and Company, Indianapolis, IN (US)

(72) Inventor: Ian Charles Smith, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 130 days.

(21) Appl. No.: 17/462,872

(22) Filed: Aug. 31, 2021

(65) Prior Publication Data

US 2021/0393630 A1 Dec. 23, 2021

Related U.S. Application Data

(63) Continuation of application No. 16/605,226, filed as application No. PCT/US2018/029289 on Apr. 25, 2018, now abandoned.

(60) Provisional application No. 62/500,068, filed on May 2, 2017.

(51) Int. Cl.

| | |
|---|---|
| ***A61K 31/506*** | (2006.01) |
| ***A61K 31/138*** | (2006.01) |
| ***A61K 31/4196*** | (2006.01) |
| ***A61K 31/5685*** | (2006.01) |
| ***A61P 35/04*** | (2006.01) |

(52) U.S. Cl.

CPC .......... *A61K 31/506* (2013.01); *A61K 31/138* (2013.01); *A61K 31/4196* (2013.01); *A61K 31/5685* (2013.01); *A61P 35/04* (2018.01)

(58) Field of Classification Search

None

See application file for complete search history.

(56) References Cited

U.S. PATENT DOCUMENTS 7,855,211 B2 12/2010 Coates et al.

OTHER PUBLICATIONS

Spring et al., Discov Med. Jan. 2016;21(113):65-74 (Year: 2016).*

Cole et al., A new anti-oestrogenic agent in late breast cancer. An early clinical appraisal of ICI46474. Br J Cancer. Jun. 1971;25(2): 270-5 (Year: 1971).*

Fisher et al., Five versus more than five years of tamoxifen for lymph node-negative breast cancer: updated findings from the National Surgical Adjuvant Breast and Bowel Project B-14 randomized trial. J Natl Cancer Inst. May 2, 2001;93(9):684-90 (Year: 2001).*

Nabholtz et al., Anastrozole is superior to tamoxifen as first-line therapy for advanced breast cancer in postmenopausal women: results of a North American multicenter randomized trial. Arimidex Study Group. J Clin Oncol. Nov. 15, 2000;18(22):3758-67 (Year: 2000).*

Howell et al., ATAC Trialists' Group. Results of the ATAC (Arimidex, Tamoxifen, Alone or in Combination) trial after completion of 5 years' adjuvant treatment for breast cancer. Lancet. Jan. 1-7, 2005;365(9453):60-2. (Year: 2005).*

Slamon et al., Use of chemotherapy plus a monoclonal antibody against HER2 for metastatic breast cancer that overexpresses HER2. N Engl J Med. Mar. 15, 2001;344(11):783-92 (Year: 2001).*

Romond et al., Trastuzumab plus adjuvant chemotherapy for operable HER2-positive breast cancer. N Engl J Med. Oct. 20, 2005;353(16):1673-84 (Year: 2005).*

Swain et al., Cleopatra Study Group. Pertuzumab, trastuzumab, and docetaxel in HER2-positive metastatic breast cancer. N Engl J Med. Feb. 19, 2015;372(8):724-34 (Year: 2015).*

Gianni et al., 5-year analysis of neoadjuvant pertuzumab and trastuzumab in patients with locally advanced, inflammatory, or early-stage HER2-positive breast cancer (NeoSphere): a multicentre, open-label, phase 2 randomised trial. Lancet Oncol. Jun. 2016;17(6):791-800. (Year: 2016).*

Burstein et al., Neratinib, an irreversible ErbB receptor tyrosine kinase inhibitor, in patients with advanced ErbB2-positive breast cancer. J Clin Oncol. Mar. 10, 2010;28(8):1301-7. (Year: 2010).*

Chan et al., ExteNET Study Group. Neratinib after trastuzumab-based adjuvant therapy in patients with HER2-positive breast cancer (ExteNET): a multicentre, randomised, double-blind, placebo-controlled, phase 3 trial. Lancet Oncol. Mar. 2016;17(3):367-377 (Year: 2016).*

Goetz, et al., Journal of Clinical Oncology, vol. 33, No. 15 Suppl., published online May 20, 2015 (Year: 2015).*

Goldhirsch et al., Annals of Oncology, vol. 20, Issue 8, 2009, pp. 1319-1329 (Year: 2009).*

Mayer et al., "Palbociclib with adjuvant endocrine therapy in early breast cancer (PALLAS): interim analysis of a multicentre, open-label, randomised, phase 3 study" Lancet Oncol. 2021; 22(2): 212-222 (Year: 2021).*

Loibl et al., "Palbociclib for Residual High-Risk HR-Positive and HER2-Negartive Early Breast Cancer—The Penelope-B Trial" J. Clin. Oncol. 2021; 39(14): 1518-1530 (Year: 2021).*

Hurvitz S et al, "late-breaking and deferred publication abstracts breast cancer, early stage", doi:10.1093/annonc/mdw435.2.

(Continued)

*Primary Examiner* — Jeffrey S Lundgren

*Assistant Examiner* — Anthony Joseph Seitz

(74) *Attorney, Agent, or Firm* — Tina M. Tyson; Joseph Pletcher

(57) ABSTRACT

The present invention discloses an adjuvant treatment of node-positive, early stage, hormone receptor-positive (HR+), human epidermal growth factor receptor 2-negative (HER2−) breast cancer comprising administering an effective amount of an endocrine therapy in combination with an effective amount of abemaciclib or a pharmaceutically acceptable salt thereof.

9 Claims, No Drawings

(56) References Cited

OTHER PUBLICATIONS

Columbus Gina, "Expert Discusses Abemaciclib Plus Anastrazole Trial in HR+/HER2-Breast Cancer", http://www.targetedonc.com/news/expert-discusses-abemaciclib-plus-anastrazole-trial-in-hrher2-breast-cancer.
Erika Hamilton et al, "Targeting CKD4/6 in patients with cancer" Cancer Treatment Reviews, vol. 45, Apr. 1, 2016 pp. 129-138, Amsterdam, NL.
Ami N. Shah et al, "The Growing Role of CDK4/6 Inhibitors in Treating Hormone Receptor-Positive Advanced Breast Cancer" Current Treatment Options inn Oncology May 2005, vol. 18, No. 1, Jan. 1, 2017, Boston.
Richard S. Finn et al, "Palbociclib and Letrozole in Advanced Breast Cancer", New England Journam of Medicine, vol. 375, No. 20, Nov. 17, 2016, pp. 1925-1936, US.
Vasconcelos Ines et al, "The St. Gallen surrogate classification for breast cancer subtypes successfully predicts tumor presenting features, nodal involvement, recurrence patterns and disease free survival", The Breast, vol. 29, Aug. 18, 2016, pp. 181-185, Edinburgh, GB.
Matthew P. Goetz et al, "Monarch 3: Abemaciclib as Initial Therapy for Advanced Breast Cancer", Journal of Clinical Oncology, vol. 35, No. 32, Nov. 10, 2017, pp. 3638-3646, US.
International Search Report for PCT/US2018/029289, Jul. 6, 2018.
Written Opinion for PCT/US2018/029289, Jul. 6, 2018.
Yamamoto-Ibusuki et al., "Targeted therapies for ER+/HER2-metastatic breast cancer," BMC Medicine, vol. 13, p. 137 (2015).
Goetz, et al., Journal of Clinical Oncology, vol. 33, No. 15 Suppl., published online (May 20, 2015).
Ma, et al., AACR San Antonio Breast Cancer Symposium (Dec. 8-12, 2015).
Gil-Gil et al., "The role of CDK4/6 inhibitors in breast cancer," The Breast 58 (2021) 160-169, available online May 25, 2021.
Johnston et al., "Abemaciclib plus endocrine therapy for hormone receptor-positive, HER2-negative, node-positive, high-risk early breast cancer (monarchE): results from a preplanned interim analysis of a randomized, open-label, phase 3 trial," Lancet Oncol 2023: 24: 77-90, published online Dec. 6, 2022.
Murphy et al., "The Role of CDK4/6 Inhibition in Breast Cancer." The Oncologist 2015; 20: 483-490, published online Apr. 15, 2015.
Rastogi et al., "Adjuvant Abemaciclib Plus Endocrine Therapy for Hormone Receptor-Positive, Human Epidermal Growth Factor Receptor 2-Negative, High-Risk Early Breast Cancer: Results From a Preplanned monarchE Overall Survival Interim Analysis, Including 5-Year Efficacy Outcomes," J. Clin. Oncol, 42:987:993, published Jan. 9, 2024.
Third Party Observations submitted into record of European Patent Application No. 18723339.0, notification date Jan. 4, 2024.
Verzenio® (abemaciclib) FDA approved label, as revised Mar. 2023.
Albain et al., "Gemcitabine Plus Paclitaxel Versus Paclitaxel Monotherapy in Patients With Metastatic Breast Cancer and Prior Anthracycline Treatment" J. Clin. Oncol. 2008; 26(24): 3950-3957.
Bachelot et al., "Everolimus Added to Adjuvant Endocrine Therapy in Patients With High-Risk Hormone Receptor—Positive, Human Epidermal Growth Factor Receptor 2-Negative Primary Breast Cancer" J. Clin. Oncol. 2022; 40(32): 3699-3708.
Baker, "2013 San Antonio Breast Cancer Symposium—News" Lancet Oncol. 2014; 15(2):138.
Baselga et al., "Everolimus in Postmenopausal Hormone-Receptor-Positive Advanced Breast Cancer" N. Engl. J. Med. 2012; 366(6): 520-529.
Bear et al., "Neoadjuvant plus adjuvant bevacizumab in early breast cancer (NSABP B-40 [NRG Oncology]): secondary outcomes of a phase 3, randomised controlled trial" Lancet Oncol. 2015; 16(9): 1037-1048.
Cameron et al., "Adjuvant bevacizumab-containing therapy in triple-negative breast cancer (BEATRICE): primary results of a randomised, phase 3 trial" Lancet Oncol. 2013; 14(10): 933-942.
Cardoso et al., "3rd ESO-ESMO International Consensus Guidelines for Advanced Breast Cancer (ABC 3)" Ann. Oncol. 2017; 28(1):16-33.
Chavez-MacGregor et al., "Phase III randomized, placebo-controlled clinical trial of adjuvant endocrine therapy +/− 1 year of everolimus in patients with high-risk hormone receptor-positive, HER2-negative breast cancer" J. Clin. Oncol. 2024; 42(25): 3012-3021.
Curtit et al., "Discordances in Estrogen Receptor Status, Progesterone Receptor Status, and HER2 Status Between Primary Breast Cancer and Metastasis" Oncologist 2013; 18(6): 667-74.
De Gregorio et al., "Gemcitabine as adjuvant chemotherapy in patients with high-risk early breast cancer-results from the randomized phase III Success—A trial" Breast Cancer Res. 2020; 22(1):111.
Earl et al., "Effects of the addition of gemcitabine, and paclitaxel-first sequencing, in neoadjuvant sequential epirubicin, cyclophosphamide, and paclitaxel for women with high-risk early breast cancer (Neo-tAnGo): an open-label, 2×2 factorial randomised phase 3 trial" Lancet Oncol. 2014; 15(2):201-212.
Earl et al., "Addition of gemcitabine to paclitaxel, epirubicin, and cyclophosphamide adjuvant chemotherapy for women with early-stage breast cancer (tAnGo): final 10-year follow-up of an open-label, randomised, phase 3 trial" Lancet Oncol. 2017; 18(6): 755-769.
Finn et al., "Palbociclib and Letrozole in Advanced Breast Cancer" N. Engl. J. Med. 2016; 375(20): 1925-1936.
Geyer et al., "Lapatinib plus Capecitabine for HER2-Positive Advanced Breast Cancer" N. Engl. J. Med. 2006; 355(26): 2733-2743.
Gharwan et al., "Kinase inhibitors and monoclonal antibodies in oncology: clinical implications" Nat. Rev. Clin. Oncol. 2016; 13, 209-227.
Goss et al., "Adjuvant lapatinib for women with early-stage HER2-positive breast cancer: a randomised, controlled phase 3 trial" Lancet Oncol. 2013; 14(1): 88-96.
Gourgou-Bourgade et al., "Guidelines for time-to-event end point definitions in breast cancer trials: results of the DATECAN initiative (Definition for the Assessment of Time-to-event Endpoints in CANcer trials)" Annals of Oncology. 2015; 26(5): 873-879.
Hudis et al., "Proposal for Standardized Definitions for Efficacy End Points in Adjuvant Breast Cancer Trials: The STEEP System" J. Clin. Oncol. 2007; 25: 2127-2132.
Johnston et al., "Overall survival with abemaciclib in early breast cancer" Annals of Oncology, vol. o, Issue o, published online Oct. 17, 2025. DOI: 10.1016/j.annonc.2025.10.005.
Krøigård et al., "Molecular Concordance Between Primary Breast Cancer and Matched Metastases" Breast J. 2016; 22 (4): 420-30.
Loibl et al., "Palbociclib for Residual High-Risk Invasive HR-Positive and HER2-Negative Early Breast Cancer—The Penelope—B Trial" J. Clin. Oncol. 2021; 39(14): 1518-1530.
Mayer et al., "Palbociclib with adjuvant endocrine therapy in early breast cancer (PALLAS): interim analysis of a multicentre, open-label, randomised, phase 3 study" Lancet Oncol. 2021; 22(2): 212-222.
Miller et al., "Paclitaxel plus Bevacizumab versus Paclitaxel Alone for Metastatic Breast Cancer" N. Engl. J. Med. 2007; 357(26): 2666-2676.
Miller et al., "Double-Blind Phase III Trial of AdjuvantChemotherapyWith and Without Bevacizumab in PatientsWith LymphNode-Positive and High-Risk Lymph Node-Negative Breast Cancer (E5103)" J Clin Oncol. 2018; 36(25): 2621-2629.
Piccart-Gebhart et al., "Adjuvant Lapatinib and Trastuzumab for Early Human Epidermal Growth Factor Receptor 2-Positive Breast Cancer: Results From the Randomized Phase III Adjuvant Lapatinib and/or Trastuzumab Treatment Optimization Trial" J. Clin. Oncol. 2016; 34(10): 1034-1042.
Reinert et al., "Optimal management of hormone receptor positive metastatic breast cancer in 2016" Ther Adv Med Oncol. Jul. 2015; 7(4): 304-320.
Royce et al., "FDA Approval Summary: Abemaciclib With Endocrine Therapy for High-Risk Early Breast Cancer" Journal of Clinical Oncology, vol. 40, No. 11, Jan. 27, 2022.

(56) References Cited

OTHER PUBLICATIONS

Ryan et al., "FDA Drug Approval Summary: Lapatinib in Combination with Capecitabine for Previously Treated Metastatic Breast Cancer That Overexpresses HER-2" Oncologist. 2008; 13(10): 1114-1119.
Swain et al., "Definitive Results of a Phase III Adjuvant Trial Comparing Three Chemotherapy Regimens in Women With Operable, Node-Positive Breast Cancer: The NSABP B-38 Trial" J. Clin. Oncol. 2013; 31(26): 3197-3204.
Anonymous, "Phase III Study Evaluating Palbociclib (PD-0332991) 'Penelope B'," ClinicalTrials.gov, NCT01864746 (XP093408579).
"Penelope-B Trial of IBRANCE® (palbociclib) in Early Breast Cancer Did Not Meet Primary Endpoint," Pfizer Inc. press release.
Gnant, Michael et al. "Adjuvant palbociclib for early breast cancer: the PALLAS trial results (ABCSG-42/AFT-05/ BIG-14-03)." Journal of Clinical Oncology 40.3 (2022): 282-293.
Third-Party Observations submitted into record of EP Application No. 18723339.0, notification date Apr. 29, 2026.
Communication pursuant to Article 94(3) EPC issued in EP Application No. 18723339.0 (EP 3 618 820).

* cited by examiner

ENDOCRINE THERAPY AND ABEMACICLIB COMBINATION FOR THE ADJUVANT TREATMENT OF NODE-POSITIVE, EARLY STAGE, HORMONE RECEPTOR-POSITIVE, HUMAN EPIDERMAL GROWTH FACTOR RECEPTOR 2-NEGATIVE BREAST CANCER

The present invention relates to the field of adjuvant treatment of node-positive, early stage, hormone receptor-positive (HR+), human epidermal growth factor receptor 2-negative (HER2−) breast cancer.

The currently approved standards of care offered to patients with node-positive, early stage, hormone receptor-positive (HR+), human epidermal growth factor receptor 2-negative (HER2−) breast cancer are adjuvant cytotoxic chemotherapy and endocrine therapy. Unfortunately, with current standard of care adjuvant therapy, approximately 30% of women with hormone receptor positive (HR+) breast cancer initially diagnosed with early stage disease experience distant relapse with metastases. Consequently, there is a critical need for more optimal adjuvant therapy in patients with early HR+ breast cancer who have a high likelihood of distant recurrence.

According to one aspect of the present invention, there is presented a method of providing adjuvant treatment to a patient with a prior diagnosis of node-positive, early stage, HR+, HER2− breast cancer which has been resected comprising administering an effective amount of an endocrine therapy in combination with an effective amount of abemaciclib or a pharmaceutically acceptable salt thereof for a time period sufficient to increase distant relapse-free survival. Preferably the endocrine therapy is tamoxifen or a pharmaceutically acceptable salt thereof. Preferable the endocrine therapy is letrozole. Preferably the endocrine therapy is anastrozole. Preferably the endocrine therapy is exemestane.

According to another aspect of the present invention, there is presented a combination comprising therapeutically effective amounts of abemaciclib, or a pharmaceutically acceptable salt thereof, and an endocrine therapy for simultaneous, separate, or sequential use in providing adjuvant treatment to a patient with a prior diagnosis of node-positive, early stage, HR+, HER2− breast cancer which has been resected, wherein administration of the abemaciclib or the salt thereof and the endocrine therapy is for a time period sufficient to increase distant relapse-free survival. Preferably the endocrine therapy is tamoxifen or a pharmaceutically acceptable salt thereof. Preferable the endocrine therapy is letrozole. Preferably the endocrine therapy is anastrozole. Preferably the endocrine therapy is exemestane.

According to another aspect of the present invention, there is presented a therapeutically effective amount of abemaciclib, or a pharmaceutically acceptable salt thereof, for use in simultaneous, separate, or sequential combination with a therapeutically effective amount of an endocrine therapy in providing adjuvant treatment to a patient with a prior diagnosis of node-positive, early stage, HR+, HER2− breast cancer which has been resected, wherein administration of the abemaciclib or the salt thereof and the endocrine therapy is for a time period sufficient to increase distant relapse-free survival. According to another aspect of the present invention, there is presented a therapeutically effective amount of an endocrine therapy for use in simultaneous, separate, or sequential combination with a therapeutically effective amount of abemaciclib, or a pharmaceutically acceptable salt thereof, in providing adjuvant treatment to a patient with a prior diagnosis of node-positive, early stage, HR+, HER2− breast cancer which has been resected, wherein administration of the abemaciclib or the salt thereof and the endocrine therapy is for a time period sufficient to increase distant relapse-free survival. Preferably the endocrine therapy is tamoxifen or a pharmaceutically acceptable salt thereof. Preferable the endocrine therapy is letrozole. Preferably the endocrine therapy is anastrozole. Preferably the endocrine therapy is exemestane.

According to another aspect of the present invention, there is also presented the use of abemaciclib, or a pharmaceutically salt thereof, in the manufacture of a medicament for providing adjuvant treatment of node-positive, early stage, HR+, HER2− breast cancer which has been resected wherein the abemaciclib, or the salt thereof, is to be administered in simultaneous, separate, or sequential combination with an endocrine therapy for a time period sufficient to increase distant relapse-free survival. Preferably the endocrine therapy is tamoxifen or a pharmaceutically acceptable salt thereof. Preferable the endocrine therapy is letrozole. Preferably the endocrine therapy is anastrozole. Preferably the endocrine therapy is exemestane.

According to another aspect of the present invention, there is also presented the use of an endocrine therapy in the manufacture of a medicament for providing adjuvant treatment of node-positive, early stage, HR+, HER2− breast cancer which has been resected wherein the endocrine therapy is to be administered in simultaneous, separate, or sequential combination with abemaciclib, or a pharmaceutically salt thereof, for a time period sufficient to increase distant relapse-free survival. Preferably the endocrine therapy is tamoxifen or a pharmaceutically acceptable salt thereof. Preferable the endocrine therapy is letrozole. Preferably the endocrine therapy is anastrozole. Preferably the endocrine therapy is exemestane.

For all of the preceding aspects, the following are preferred dosing. Preferably, abemaciclib, or the pharmaceutically salt thereof, is administered at a dose of 50 mg to 200 mg twice a day. Also preferably, abemaciclib, or the pharmaceutically salt thereof, is administered at a dose of 100 mg to 150 mg twice a day. More preferably, abemaciclib, or the pharmaceutically salt thereof, is administered at a dose of 200 mg twice a day. More preferably, abemaciclib, or the pharmaceutically salt thereof, is administered at a dose of 150 mg twice a day in a 28-day cycle. More preferably, abemaciclib, or the pharmaceutically salt thereof, is administered at a dose of 100 mg twice a day in a 28-day cycle. More preferably, abemaciclib, or the pharmaceutically salt thereof, is administered at a dose of 50 mg twice a day in a 28-day cycle. Preferably, abemaciclib is administered orally. More preferably, abemaciclib is administered by capsule. Also more preferably, abemaciclib is administered by tablet.

Preferably, an endocrine therapy is administered as described on the approved label of the particular endocrine therapy. For example, tamoxifen or a pharmaceutically acceptable salt thereof may be administered at 20-40 mg/day. For doses over 20 mg, the dose should be administered in a divided dose of morning and evening. Doses are preferably oral. For example, anastrazole may be administered at 1 mg/day. Doses are preferably oral. For example, letrozole may be administered at 2.5 mg/day. Doses are preferably oral. For example, exemestane may be administered at 25 mg/day. Doses are preferably oral.

Preferably, tamoxifen or a pharmaceutically acceptable salt thereof is administered at 20-40 mg/day and abemaciclib or a pharmaceutically acceptable salt thereof is administered at 200 mg twice daily. Preferably, tamoxifen or a pharmaceutically acceptable salt thereof is administered at 20-40 mg/day and abemaciclib or a pharmaceutically acceptable salt thereof is administered at 150 mg twice daily. Preferably, tamoxifen or a pharmaceutically acceptable salt thereof is administered at 20-40 mg/day and abemaciclib or a pharmaceutically acceptable salt thereof is administered at 100 mg twice daily. For doses of tamoxifen or a salt thereof over 20 mg, the dose should be administered in a divided dose of morning and evening. Doses are preferably oral for both tamoxifen or the salt thereof and abemaciclib or the salt thereof.

Preferably, anastrazole is administered at 1 mg/day and abemaciclib or a pharmaceutically acceptable salt thereof is administered at 200 mg twice daily. Preferably, anastrazole is administered at 1 mg/day and abemaciclib or a pharmaceutically acceptable salt thereof is administered at 150 mg twice daily. Preferably, anastrazole is administered at 1 mg/day and abemaciclib or a pharmaceutically acceptable salt thereof is administered at 100 mg twice daily. Doses are preferably oral for both anastrazole and abemaciclib or the salt thereof.

Preferably, letrozole is administered at 2.5 mg/day and abemaciclib or a pharmaceutically acceptable salt thereof is administered at 200 mg twice daily. Preferably, letrozole is administered at 2.5 mg/day and abemaciclib or a pharmaceutically acceptable salt thereof is administered at 150 mg twice daily. Preferably, letrozole is administered at 2.5 mg/day and abemaciclib or a pharmaceutically acceptable salt thereof is administered at 100 mg twice daily. Doses are preferably oral for both anastrazole and abemaciclib or the salt thereof.

Preferably, exemestane is administered at 25 mg/day and abemaciclib or a pharmaceutically acceptable salt thereof is administered at 200 mg twice daily. Preferably, exemestane is administered at 25 mg/day and abemaciclib or a pharmaceutically acceptable salt thereof is administered at 150 mg twice daily. Preferably, exemestane is administered at 25 mg/day and abemaciclib or a pharmaceutically acceptable salt thereof is administered at 100 mg twice daily. Doses are preferably oral for both anastrazole and abemaciclib or the salt thereof.

As used herein, the term "patient" refers to a human.

As used herein, the terms "cancer" and "cancerous" refer to or describe the physiological condition in patients that is typically characterized by unregulated cell proliferation.

As used herein, the term "effective amount" refers to the amount or dose of abemaciclib, or a pharmaceutically acceptable salt thereof, and the amount or dose of an endocrine therapy which provides an effective response in the patient under diagnosis or treatment.

As used herein, the term "effective response" of a patient or a patient's "responsiveness" to treatment with a combination of agents refers to the clinical or therapeutic benefit imparted to a patient upon administration of abemaciclib, or a pharmaceutically acceptable salt thereof, and an endocrine therapy.

As used herein, the term "in combination with" refers to the administration of abemaciclib, or a pharmaceutically acceptable salt thereof, and an endocrine therapy either simultaneously or sequentially in any order, such as for example, at repeated intervals as during a standard course of treatment for a single cycle or more than one cycle, such that one agent can be administered prior to, at the same time, or subsequent to the administration of the other agent, or any combination thereof.

Abemaciclib (LY2835219), [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, is a CDK inhibitor that targets the CDK4 and CDK6 cell cycle pathway, with antineoplastic activities. Abemaciclib, including salt forms, and methods of making and using this compound including for the treatment of cancer, in particular, breast cancer are disclosed in WO2010/075074. Abemaciclib has the following structure:

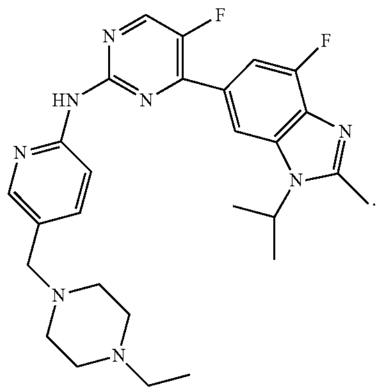 [SMILES: CCN1CCN(Cc2ccc(Nc3ncc(F)c(-c4cc(F)c5nc(C)n(C(C)C)c5c4)n3)nc2)CC1]

Abemaciclib showed antitumor activity within multiple preclinical pharmacology models and an acceptable toxicity profile in nonclinical species. Abemaciclib has been shown to significantly inhibit tumor growth in multiple murine xenograft models for human cancer, including breast cancer. Growth inhibition in vitro across a diverse panel of 46 breast cancer cell lines, representing the known molecular subgroups of breast cancer, indicates that sensitivity to CDK4 and CDK6 inhibition is greater in ER+ breast cancers with luminal histology.

Continuously dosed abemaciclib has demonstrated robust single-agent clinical activity in both the JPBA Phase 1b study with a response rate of 33.3% across dose levels and the MONARCH 1 Phase 2 study with a response rate of 19.7% (at 200-mg dose twice daily), in patients with heavily pretreated HR+ metastatic breast cancer that is refractory to endocrine therapy (Patnaik et al. 2016; Dickler et al. 2016).

When combined with standard endocrine therapies (for example, tamoxifen, letrozole, anastrozole, exemestane), abemaciclib demonstrated early evidence of antitumor activity against HR+ mBC (objective response rate: 10% to 40%; disease control rate: 60% to 87.5%) and was tolerable in the ongoing JPBH Phase 1b study (Beeram et al. 2016). In JPBH, the most common adverse events (AEs) experienced by patients receiving abemaciclib plus endocrine therapy included fatigue, nausea, diarrhea, leukopenia, lymphopenia, neutropenia, and anemia, which are predominantly of low-grade severity and appear to be dose-dependent.

In early neoadjuvant breast cancer setting, the ongoing neoMONARCH Phase 2 open-label, randomized study (I3Y-MC-JPBY) showed an acceptable safety profile for abemaciclib (150 mg twice daily) as monotherapy and in combination with anastrozole, with reduction of breast cancer tumor cell proliferation marker (Ki67 index) to a significantly greater extent than anastrozole alone (Hurvitz et al. 2016).

As used herein, the term "endocrine therapy" means tamoxifen or a pharmaceutically acceptable salt thereof, anastrozole, letrozole, or exemestane.

Tamoxifen is a selective estrogen receptor modulators (SEAM) with tissue-specific activities for the treatment and prevention of estrogen receptor positive breast cancer. Tamoxifen acts as an anti-estrogen (inhibiting agent) in the mammary tissue, but as an estrogen (stimulating agent) in cholesterol metabolism, bone density, and cell proliferation in the endometrium. Tamoxifen has the following structure:

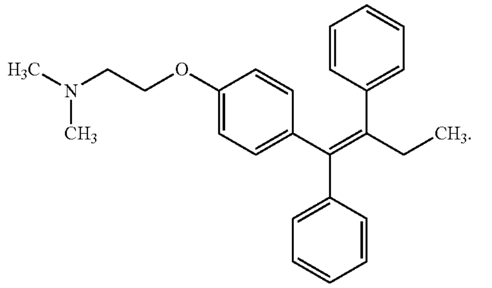 [SMILES: CC/C(=C(\c1ccccc1)c1ccc(OCCN(C)C)cc1)c1ccccc1]

Anastrozole is a drug indicated in the treatment of breast cancer in postmenopausal women. It is used both in adjuvant therapy (i.e. following surgery) and in metastatic breast cancer. It decreases the amount of estrogens that the body makes. Anastrozole belongs in the class of drugs known as aromatase inhibitors. It inhibits the enzyme aromatase, which is responsible for converting androgens (produced by women in the adrenal glands) to estrogens. Anastrozole has the following structure:

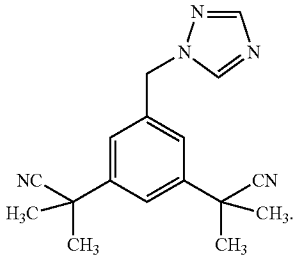 [SMILES: CC(C)(C#N)c1cc(Cn2cncn2)cc(C(C)(C)C#N)c1]

Letrozole is an oral non-steroidal aromatase inhibitor that has been introduced for the adjuvant treatment of hormonally-responsive breast cancer. Letrozole has the following structure:

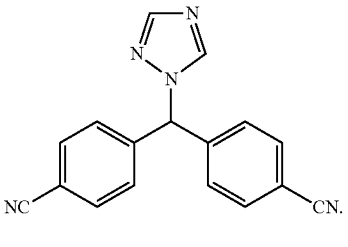 [SMILES: N#Cc1ccc(C(c2ccc(C#N)cc2)n2cncn2)cc1]

Exemestane is an oral steroidal aromatase inhibitor used in the adjuvant treatment of hormonally-responsive (also called hormone-receptor-positive, estrogen-responsive) breast cancer in postmenopausal women. It acts as a false substrate for the aromatase enzyme, and is processed to an intermediate that binds irreversibly to the active site of the enzyme causing its inactivation. Exemestane has the following structure:

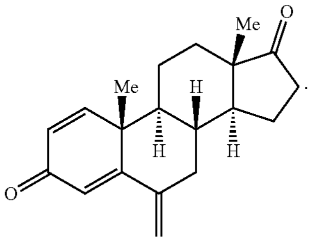

As used herein, the term "resection" means surgical removal of malignant tissue characteristic of breast cancer from a patient. According to one embodiment, resection means removal of malignant tissue such that the presence of remaining malignant tissue within said patient is undetectable with available methods. According to another embodiment of the invention resection means removal of breast cancer such that the presence of remaining breast cancer with said patient is undetectable.

As used herein, the term "distant relapse-free survival" means the time from starting treatment of the combination of abemaciclib or the salt thereof and the endocrine therapy to disease recurrence, distant metastases, or death from any cause.

As used herein, the term "early stage" means cancers that may have spread to nearby lymph nodes but not to distant parts of the body.

As used herein, the term "treating", "treatment", or adjuvant treatment" means the administration of a drug or drugs to a patient after surgical resection of one or more cancerous tumors, where all detectable and resectable disease (for example, cancer) has been removed from the patient, but where there remains a statistical risk of relapse due to occult disease, for the purpose of diminishing the likelihood or the severity of reoccurrence of the disease, or to delay the onset of the biological manifestation of the reoccurrence of the disease.

"Ki67 antigen" or simply "Ki67" (also known as antigen identified by monoclonal antibody Ki-67) means a nuclear protein encoded by the MKI67 gene that is expressed in all phases of the cell cycle other than the G0 phase and has been reported as an independent prognostic factor in early breast cancer (Dowsett et al. 2011). In HR+ breast cancer, patients with high levels of Ki67 have been shown to have higher disease recurrence rates while receiving adjuvant endocrine therapy following surgery. In the BIG 1-98 study (Viale et al. 2008), patients receiving letrozole with HR+ early breast cancer involving their axillary lymph nodes and low (≤11%) Ki67 levels at baseline had a 4-year disease-free survival of 93% compared to 85% for patients with higher Ki67 values (>11%). Currently, there is no consensus as to the precise baseline level of Ki67 that would differentiate a patient for being of higher or lower risk of disease recurrence whilst on adjuvant endocrine therapy. However, the majority of the panel of the St Gallen International Expert Consensus on the Primary Therapy of Early Breast Cancer 2015 was prepared to accept a threshold value of Ki67 within the range of 20% to 29% (Vasconcelos et al. 2016) as indicative of high-risk group appropriate to receive adjuvant chemotherapy.

EXAMPLE 1

A Randomized, Open-Label, Phase 3 Study of Abemaciclib Combined with Standard Adjuvant Endocrine Therapy Versus Standard Adjuvant Endocrine Therapy Alone in Patients with High Risk, Node Positive, Early Stage, Hormone Receptor Positive, Human Epidermal Receptor 2 Negative, Breast Cancer The primary objective of this study is to evaluate the efficacy, in terms of invasive disease-free survival (IDFS), as defined by the STEEP System, for patients with HR+, HER2− early stage breast cancer for abemaciclib 150 mg twice daily plus adjuvant endocrine therapy versus adjuvant endocrine therapy alone.

The secondary objectives of this study is to
- evaluate the efficacy, in terms of IDFS, for patients with HR+, HER2− early stage breast cancer with Ki67 index≥20% (both Cohort 1 and Cohort 2 by central lab);
- evaluate the efficacy of abemaciclib plus adjuvant endocrine therapy versus adjuvant endocrine therapy alone in terms of distant relapse-free survival (DRFS) and overall survival (OS);
- assess the safety profile of abemaciclib plus adjuvant endocrine therapy compared to adjuvant endocrine therapy alone;
- evaluate the relationship between abemaciclib exposure and clinical (efficacy and safety) outcomes;
- evaluate abemaciclib plus adjuvant endocrine therapy, versus adjuvant endocrine therapy alone, in terms of general oncology and breast cancer self-reported health-related quality of life (Functional Assessment of Cancer Therapy [FACT]-Breast 37-item questionnaire), endocrine therapy-specific symptoms (Functional Assessment of Cancer Therapy-Endocrine Symptoms (Version 4) [FACT-ES] 19-item subscale and 2 Functional Assessment of Chronic Illness Therapy Item Library [FACIT] (Version 2) sourced items of cognitive symptoms and 3 FACIT-sourced items for bladder symptoms), and fatigue experienced during abemaciclib and/or endocrine therapy (FACIT-Fatigue 13-item subscale); and
- evaluate health status to inform decision modeling for health economic evaluation using the EuroQol five-dimension five-level questionnaire.

The study will screen approximately 4200 patients, and approximately 3580 patients will be enrolled and subdivided into 2 cohorts: those eligible based on nodal status, tumor size, or grade regardless of Ki67 status, Cohort 1, and those with at least 1 positive node and eligible exclusively based on a Ki67 status, Cohort 2 (that is, those patients not eligible based on tumor size or grade). Cohort 1 will enroll approximately 3080 patients and Cohort 2 will enroll approximately 500 patients.

Patients in both treatment arms will receive standard adjuvant endocrine therapy of physician's choice (such as tamoxifen or an aromatase inhibitor, with or without ovarian function suppression per standard practice). Patients in both arms may have started standard adjuvant endocrine therapy within 8 weeks prior to randomization, and the same or another endocrine therapy will be continued during the course of the study and in the absence of disease recurrence. Consistent with standard guidelines, aromatase inhibitor should be at least part of endocrine therapy for postmenopausal patients. Adjuvant treatment with fulvestrant is not allowed at any time during the study. Randomization must occur no more than 12 weeks after completion of last non-endocrine therapy (surgery, or chemotherapy or radiotherapy). Patients randomized to the experimental arm will receive abemaciclib orally at 150 mg twice daily for up to 2 years or until evidence of disease recurrence or other discontinuation criteria are met, whichever occurs first. Endocrine therapy will be taken as prescribed during the on-study treatment period. (Years 1 and 2). In Year 3 and beyond, standard adjuvant endocrine therapy will continue to complete at least 5 years per investigator's discretion as part of standard of care.

I claim:

1. A method of adjuvant treatment of node-positive, early stage, hormone receptor-positive (HR+), human epidermal growth factor receptor 2-negative (HER2−) breast cancer in a patient, comprising administering to the patient an effective amount of an endocrine therapy in combination with an effective amount of abemaciclib or a pharmaceutically acceptable salt thereof, wherein the patient is treated for 2 years or until evidence of disease recurrence or other discontinuation criteria are met, whichever occurs first.

2. The method of claim 1, wherein the patient has a Ki67 index≥20%.

3. The method of claim 1, wherein the endocrine therapy is tamoxifen or a pharmaceutically acceptable salt thereof, or an aromatase inhibitor.

4. The method of claim 1, wherein the endocrine therapy is tamoxifen or a pharmaceutically acceptable salt thereof.

5. The method of claim 1, wherein the endocrine therapy is letrozole.

6. The method of claim 1, wherein the endocrine therapy is anastrozole.

7. The method of claim 1, wherein the endocrine therapy is exemestane.

8. The method of claim 1, wherein the abemaciclib or pharmaceutically acceptable salt thereof is administered at 150 mg twice daily.

9. The method of claim 1, wherein the abemaciclib or pharmaceutically acceptable salt thereof is administered at 100 mg twice daily.

* * * * *